(12) United States Patent
Harrison et al.

(10) Patent No.: US 7,574,898 B2
(45) Date of Patent: Aug. 18, 2009

(54) VIBRATING WIRE VISCOSITY SENSOR

(75) Inventors: Christopher Harrison, Auburndale, MA (US); Isabelle Etchart, Paris (FR); Kai Hsu, Sugar Land, TX (US); Jacques Jundt, Newton Highlands, MA (US); Anthony Robert Holmes Goodwin, Sugar Land, TX (US); Sophie Godefroy, Kanagawa (JP); Matthew Sullivan, Belmont, MA (US); Antoine Fornari, Boulogne-Billancourt (FR)

(73) Assignee: Schlumberger Technology Corporation, Cambridge, MA (US)

( * ) Notice: Subject to any disclaimer, the term of this patent is extended or adjusted under 35 U.S.C. 154(b) by 0 days.

(21) Appl. No.: 11/937,035

(22) Filed: Nov. 8, 2007

(65) Prior Publication Data

US 2009/0120171 A1    May 14, 2009

(51) Int. Cl.
*G01N 11/00* (2006.01)
(52) U.S. Cl. .................... 73/54.41; 73/54.02; 73/54.24; 73/54.25
(58) Field of Classification Search .............. 73/54.02, 73/54.14, 54.23–54.27, 54.41
See application file for complete search history.

(56) References Cited

U.S. PATENT DOCUMENTS 4,292,673 A * 9/1981 Du Bae .................. 702/54

7,194,902 B1  3/2007 Goodwin et al.
7,222,671 B2  5/2007 Caudwell et al.
2006/0008382 A1  1/2006 Salamitou et al.

FOREIGN PATENT DOCUMENTS

GB    2421573 A  * 6/2006    ............. 73/152.24

OTHER PUBLICATIONS

Kandil, M. "The Development of A Vibrating Wire Viscometer and A Microwave Cavity Resonator: For the Measurement of Viscosity, Dew Points, Density, and Liquid Volume Fraction At High Temperature and Pressure", Thesis, 2005, pp. 1 and 21-24.*
Tough, J.T. et al., "Vibrating Wire Viscometer" The Review of Scientific Instruments, vol. 35, No. 10, Oct. 1964, pp. 1345-1348.*
Assael et al., An Absolute Vibrating-Wire Viscometer for Liquids at High Pressures, International Journal of Thermophysics, vol. 12, No. 2, 1991, pp. 231-244.

(Continued)

*Primary Examiner*—Daniel S Larkin
(74) *Attorney, Agent, or Firm*—Vincent Loccisano; James McAleenan

(57) ABSTRACT

A method and apparatus for providing, e.g., identifying or determining, at least one parameter of a fluid moving through a fluid channel using a vibrating wire in contact with the fluid moving through the fluid channel that is clamped under tension. The vibrating wire is actuated by an actuating device capable of displacing the vibrating wire from an initial position. An interpretation element further is utilized to provide a parameter of the fluid moving through the fluid channel based upon data from the vibrating wire following actuation by the actuation element.

33 Claims, 10 Drawing Sheets

OTHER PUBLICATIONS

Padua et al., A Vibrating-Wire Densimeter for Liquids at High Pressures: The Density of 2,2,4-Trimethylpentane from 298.15 to 348.15 K and up to 100 MPa, International Journal of Thermophysics, vol. 15, No. 2, 1994, pp. 229-243.

Padua et al., Validation of an Accurate Vibrating-Wire Densimeter: Density and Viscosity of Liquids Over Wide Ranges of Temperature and Pressure, International Journal of Thermophysics, vol. 17, No. 4, 1996, pp. 781-802.

Retsina et al., The theory of a vibrating-rod viscometer, Applied Scientific Research, vol. 43, 1987, pp. 325-346.

Retsina et al., The theory of a vibrating-rod densimeter, Applied Scientific Research, vol. 43, 1986, pp. 127-158.

Audonnet et al., Simultaneous measurement of density and viscosity of n-pentane from 298 to 383 K and up to 100 MPa using a vibrating-wire instrument, Fluid Phase Equilibria, vol. 181, 2001, pp. 147-161.

Padua et al., Electormechanical model for vibrating-wire instruments, Review of Scientific Instruments, vol. 69, No. 6, 1998, pp. 2392-2399.

* cited by examiner

VIBRATING WIRE VISCOSITY SENSOR

BACKGROUND OF THE INVENTION

1. Field of the Invention

The present invention relates generally to the measurement of a property of a fluid, and more particularly the measurement of a property such as but not limited to viscosity of a fluid in a reservoir. For the purpose of clarity the present invention addresses hydrocarbon reservoirs and production setting, but is applicable to a variety of reservoir applications.

2. Background of the Invention

Measurement of a physical property of a gas, or liquid or fluid has numerous applications in residential and commercial settings. One such physical property of interest may be the viscosity of the fluid, which is central to a variety of industries and applications, including hydrocarbon production and exploration. Measurement of the physical properties of a fluid may be beneficial in gas flows, liquid flows or some combination of both gas and liquid flow. Furthermore, the flow may be a single phase or multi-phase flow. While these various flows span numerous applications, one such environment and application is the oil and natural gas industry.

In some applications within the oil and natural gas industry, knowledge of the physical properties of a fluid are beneficial in both surface based experiments as well as measurements conducted in a downhole environment. For example, in a hydrocarbon bearing reservoir setting the economic value of the hydrocarbon reserves, the efficiency of recovery, and the design of production systems all depend upon the physical properties of the reservoir hydrocarbon fluid. In such a setting, viscosity measurements are beneficial in firstly determining if it is economically viable to develop this reservoir, and, secondly to design and plan the reservoir development.

Additionally, in a downhole environment the naturally occurring hydrocarbon fluids may include dry natural gas, wet gas, condensate, light oil, black oil, heavy oil, and heavy viscous tar. Furthermore, there may be flows of water and of synthetic fluids, such as oils used in the formulation of drilling muds, fluids used in formation fracturing jobs etc. Each of these individual fluids presents vastly different physical properties, yet all may pass through a single flow channel for measurement. As general production of hydrocarbon fluids is almost always accompanied by the production of water; direct physical measurements on production fluid properties typically results in the measurement of a mixture of phases thereby resulting in a volume-averaged data. For a well producing ten barrels of water for one barrel of oil, it is therefore a challenge to obtain the true viscosity of the hydrocarbon produced, as such measurements are typically dominated by the properties of the majority phase, namely that of water.

As the economic value of a hydrocarbon reserve, the method of production, the efficiency of recovery, the design of production hardware systems, etc., all depend upon a number physical properties of the encountered fluid, it is important that these physical properties are determined accurately.

Several measurement principles have been attempted in the past to measure the viscosity of flowing fluids encountered in the hydrocarbon industry and other industries, but each technique has associated weaknesses. One such technique uses NMR measurements wherein the viscosity of reservoir fluids can be deduced, but the accuracy is usually considered to be no better than an order of magnitude without additional modification of the interpretation based on information concerning the local oilfield environment. For incompressible fluids the viscosity can be accurately measured granted a known flown rate and the pressure drop along a flow line, but flow rate measurements are notorious for being inaccurate, decreasing the accuracy of the viscosity measurement.

In view of the foregoing limitations of traditional techniques, a measurement apparatus for providing, e.g., identifying or determining, at least one parameter of a fluid moving in a fluid channel using a vibrating wire is beneficial.

SUMMARY OF THE INVENTION

The present invention recites a vibrating wire based method, system and apparatus for providing, e.g., identifying or determining, at least one parameter of a fluid moving through a fluid channel. Such techniques, method and apparatus have been recited in the prior art, including in U.S. Pat. No. 7,194,902, Apparatus and method for formation evaluation, and U.S. Pat. No. 7,222,671, Apparatus and method for formation evaluation, herein incorporated by reference.

The method, system and apparatus comprises a vibrating wire located within a fluid channel, wherein the vibrating wire is held in tension between two locating points. Furthermore, associated with the vibrating wire is an actuating device and an interpretation element, wherein the interpretation element is capable of providing, e.g., identifying or determining, a parameter of the fluid moving through the fluid channel, or microfluidic channel, based upon data from the resonating element upon actuation by the actuating device. In accordance with the present invention, the fluid parameters provided by the interpretation element may be fluid viscosity. Additionally, actuation of the device associated with the vibrating wire may be carried out in an electromagnetic field.

DETAILED DESCRIPTION OF THE INVENTION

Figure 1:
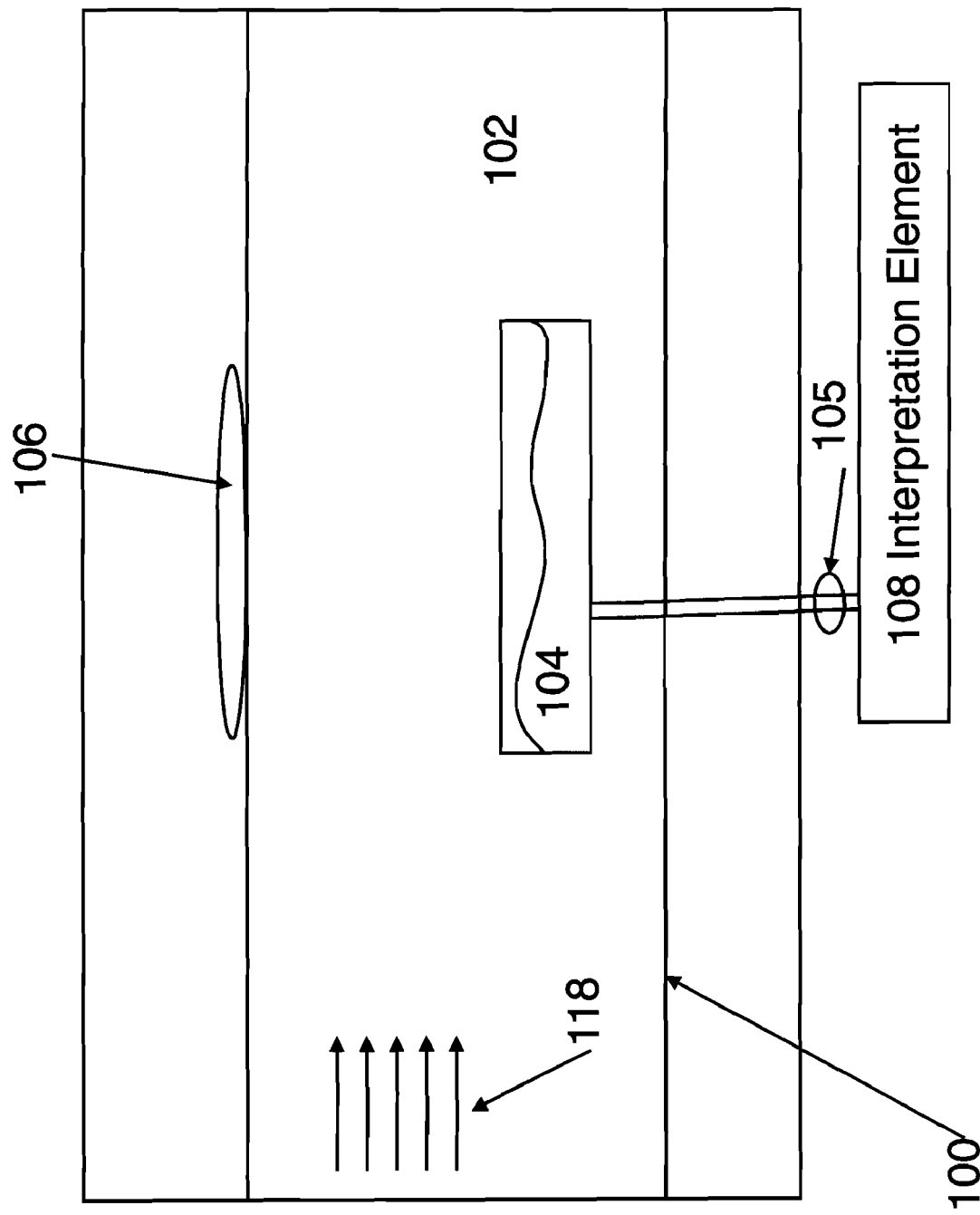
FIG. 1 is an illustrative example of one embodiment of the present invention for use in measuring a fluid parameter of a flowing fluid.

Various embodiments and aspects of the invention will now be described in detail with reference to the accompanying Figures. This invention is not limited in its application to the details of construction and the arrangement of components set forth in the following description or illustrated in the drawings. The invention is capable of various alternative embodiments and may be practiced using a variety of other ways. Furthermore, the terminology and phraseology used herein is solely used for descriptive purposes and should not be construed as limiting in scope. Language such as "including," "comprising," "having," "containing," or "involving," and variations herein, are intended to encompass the items listed thereafter, equivalents, and additional items not recited. As used herein the term "fluid channel" shall include any element capable of containing a fluid regardless of cross sectional shape.

The present invention recites a vibrating wire based method, system and apparatus for providing, e.g., identifying or determining, at least one parameter of a fluid moving through a fluid channel. The method, system and apparatus comprises a vibrating wire located within a fluid channel, wherein the vibrating wire is held in tension between two locating points. Furthermore, associated with the vibrating wire is an actuating device and an interpretation element, wherein the interpretation element is capable of providing, e.g., identifying or determining, a parameter of the fluid moving through the fluid channel, or microfluidic channel, based upon data from the resonating element upon actuation by the actuating device.

The present invention may take numerous forms and sizes. For example, the present invention may be constructed on a microfluidic level for measuring flows through a microfluidic channel, or may be a sized to measure high volumetric flows encountered in a hydrocarbon production environment. In the preferred embodiment of this invention, the parameter of interest may be fluid viscosity. While the present invention is applicable to a variety of single phase and multiphase fluids, for clarity a flowing hydrocarbon fluid will be discussed. Such a selection is not intended to be limiting in scope, as one skilled in the art will readily recognize that the methods and techniques of the present invention are applicable to a variety of industries, applications and fluids.

As illustrated in FIG. 1, a flowing fluid 102 contained within a fluid channel 100 is illustrated. In the present illustration, this fluid has a fluid direction 118. This flowing fluid may be a single phase fluid or may be a multi-phase fluid. Furthermore, the fluid channel 100 may be a macro fluid channel or may be a microfluidic fluid channel or may be incorporated into a microfluidic platform of a downhole drilling tool or assembly. For the purpose of clarity, the present invention will be described in relation to a macrofluidic fluid channel, such as the macrofluidic channel illustrated in FIG. 2. One skilled in the art will recognize that the present invention is readily applicable to a variety of fluid channels of varying size, shape and length. Disposed within the fluid channel 100 of the present invention is a vibrating wire 104, wherein said vibrating wire 104 is immersed in the fluid 102 moving through the fluid channel 100. Furthermore the vibrating wire 104 includes an actuating device 106 associated with the vibrating wire 104. In one embodiment the actuating device may be an electromagnetic source located external to the fluid channel and capable of imparting a displacement within the vibrating wire 104. One skilled in the art will readily recognize, however, that the actuation element 106 may take numerous alternative locations, as the embodiment illustrated is for illustrative purposes only. The vibrating wire 104 may be held in tension between two anchoring points (not shown) and may take numerous orientations and embodiments. Furthermore, in accordance with one embodiment of the present invention, the vibrating wire may be a tungsten wire with a radius of about 75 μm, wherein said wire is mounted in a holder capable of providing electrical connections at each end of the wire. This holder is designed so that all current must pass through the wire and no current can pass through the holder itself. Other embodiments can include wire radii with greater or smaller dimensions as dictated by the viscosity range of interest.

The orientation and embodiment pictured herein is solely for illustration and is not intended to be limiting in scope. Further associated with the vibrating wire 104 is an interpretation element 108 wherein said interpretation element provides, e.g., identifies or determines, a parameter of the fluid 102 moving through the fluid channel 100 based upon data from the vibrating wire 104 upon actuation by the actuation device 106. The interpretation element 108 of the present embodiment is in communication with the vibrating wire 104 via a communication pathway 105. In one embodiment the communication pathway 105 may be an electrical connection, a optical connection or an acoustic connection. Additionally, additional elements such as but not limited to function generators or amplifiers may be in communication with the vibrating wire 104 using a similar communication pathway 105.

One skilled in the art will readily recognize that the present invention may be incorporated into a variety of fluid channels, including but not limited to an evaluation flowline in a downhole tool.

In accordance with one embodiment of the present invention, the vibrating wire 104 immersed in the fluid channel 100 can be used to measure the viscosity of the moving fluid. The vibrating wire 104 of the present invention may be manufactured from an electrically conductive material such that it is capable of displacement from an initial position when current is passed through it in the presence of a magnetic field provided by the actuating device 106. The motion of the vibrating wire 104 can be determined from measurements of the motional electromotive force (emf), a small voltage that develops as a result of the temporal change of the magnetic flux passing through a loop partially defined by the location of the vibrating wire 104.

The vibrating wire 104 motion can be excited and detected by a variety of methods as understood by one skilled in the art. In accordance with one technique the current passed through the conductive vibrating wire 104 is swept through a resonance of the vibrating wire 104 and the emf is measured at each frequency. Such a technique is known as a steady state approach to determining a fluid parameter. In accordance with an alternative embodiment, the vibrating wire 104 may be driven from the stationary and equilibrium initial position and the attenuation of the motion is measured as function of time. For the purposes of clarity, this will be described in greater detail as the transient approach to providing, e.g., identifying or determining, a fluid parameter.

One skilled in the art will recognize that the vibrating wire of the present embodiment may take numerous sizes, shapes and orientations for use in a variety of fluid channels encountered in a variety of applications. In accordance with one embodiment, the vibrating wire measurement apparatus of the present invention may be sized such that it uses MEMS fabrication techniques thereby providing a means by which parameter measurements may be scaled down to extremely small fluidic channels, such as those present in micro fluidic devices. In one embodiment of the present invention, a MEMS based measurement apparatus may be integrated with other existing sensors in a "lab on a chip" approach. Suitable "Lab on a Chip" systems are detailed in U.S. Patent Application Publication Number US-2006-0008382-A1, filed Jul. 6, 2004 and assigned to Schlumberger Technology Corporation, which is herein incorporated by reference. As recited earlier, however, the present invention is directly applicable to both macro and micro fluidic channels, and the illustrated MEMS device is not intended to be limiting in scope of the present invention.

Figure 2:
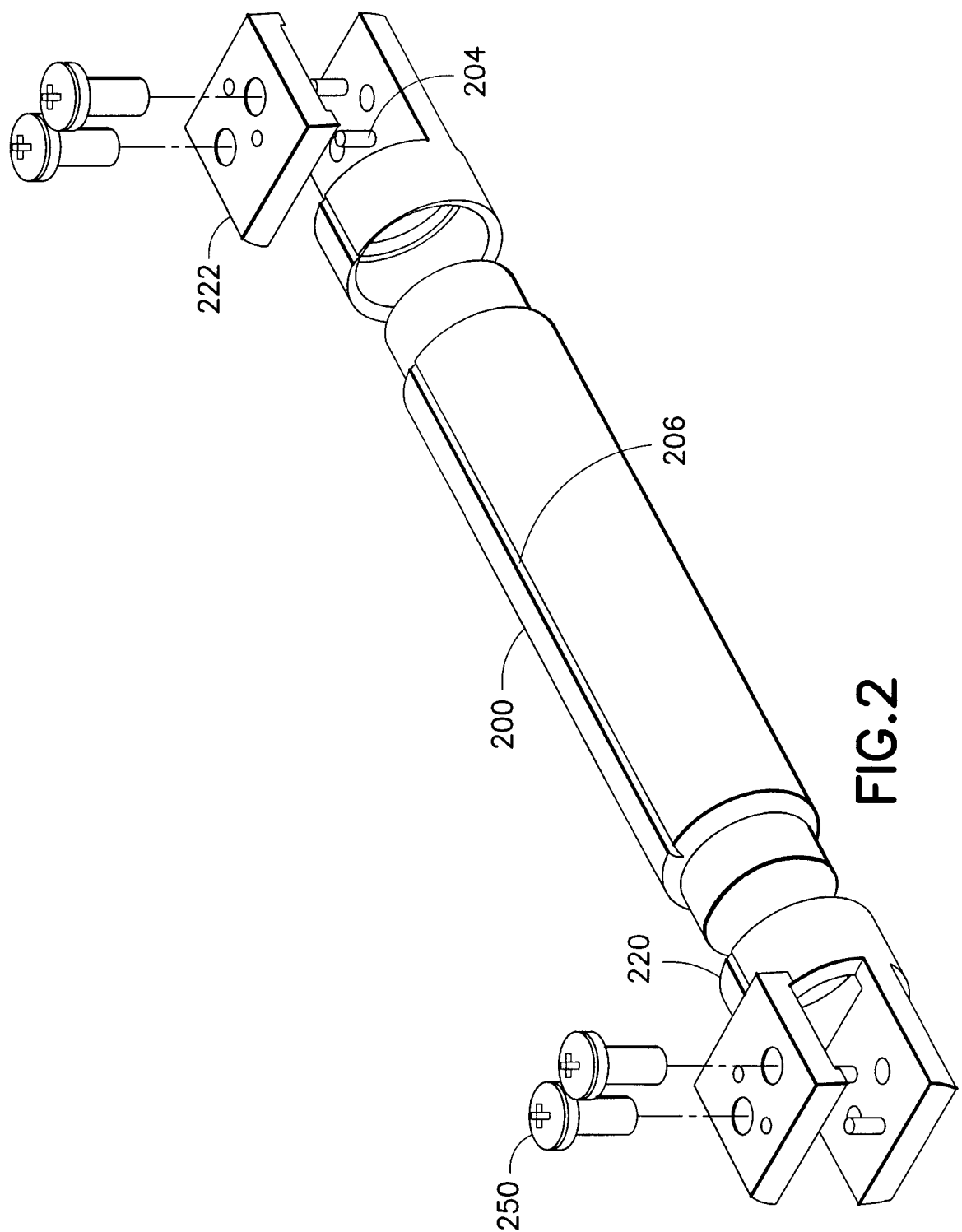
FIG. 2 is an illustrative example of an alternative embodiment of the present invention for use in measuring a fluid parameter of a flowing fluid in a microfluidic channel.

FIG. 2 is an illustrative example of a vibrating wire for use in accordance with the present invention. As illustrated in FIG. 2, the vibrating wire 204 of the present invention may be manufactured from a thin metallic wire clamped under tension between two fixed supports 220, 222 having fastening means 250 and immersed in a fluid (not shown) contained within a fluid channel 200. The vibrating wire 204 may be conductive in nature such that a current or signal, such as an actuation signal, can be applied to a portion of the vibration wire, or applied across the entire length of the vibrating wire.

In accordance with one embodiment, the actuating device 206 capable of displacing the vibrating wire 204 from an initial, or equilibrium, position may include an electromagnetic field (not shown) applied in the vicinity of the vibrating wire 204 and an actuation signal applied to at least a portion of the vibrating wire (not shown). For the purpose of clarity, an actuating device 206 capable of providing an electromagnetic field to the region surrounding the vibrating wire and an actuating signal applied to at least a portion of the vibrating wire will be described in detail. Such a description is solely for clarity and ease in describing the present invention, and the recited arrangement is not intended to be limiting in scope.

Additionally, the determination of the fluid parameters viscosity with the prior knowledge of density by the interpretation element will be discussed as applied to the present invention. One skilled in the art will recognize that the fluid parameters of density and viscosity are not an exhaustive list of parameters and the recitation of such is not intended to be limiting in scope.

In accordance with the present invention, the magnetic field used to displace or drive the vibrating wire may be a steady state field or a transient field, such that the vibrating wire 204 is driven in a steady state mode or a transient mode. In the steady state mode, a transverse oscillation of the vibrating wire 204 may be excited by continuously passing alternating current through it whereas the oscillation in the transient mode may be excited by either a short burst of alternating current or application of a dc signal, both providing the initial displacement of wire from its equilibrium position. Both transient and steady state embodiments directly applicable to the present invention, and the selection of the appropriate drive mechanism is dictated in part by the intended parameters to be measured and the fluid within the flow channel as understood by one skilled in the art.

The motion of the wire can then be determined from measurements of the voltage that is induced as a result of the temporal change of the magnetic flux passing through a loop partially defined by the location of the wire (motional emf) following actuation by the actuation device.

In the transient mode, the induced voltage V(t) developed across the wire is a short-lived oscillation that varies as a function of time and conforms to a simple damped harmonic model for small amplitude $$V(t) = V_0 e^{-\Delta \omega t} \sin(\omega t + \phi_0) \qquad \text{Eq. (1)}$$

where $V_0$ is the initial amplitude of the transient, $\Delta$ is the decrement controlling the damping of the motion, $\omega$ is the angular resonance frequency of wire and $\phi$ is the unknown phase angle. It is worth mentioning that the logarithmic decrement, a common parameter for characterizing the energy loss of a resonator, simply equals $2\pi\Delta$. We will refer to $\Delta$ as the decrement (opposed to the logarithmic decrement) as this has been often done in the literature concerning the vibrating wire (e.g. M. J. Assael, M. Papadaki, M. Dix, S. M. Richardson, W. A. Wakeham, International Journal of Thermophysics, Volume 12, #2, 1991,). In Equation (1), the decrement $\Delta$ is related to the properties of both the wire and fluid that surrounds it by $$\Delta = \frac{(\rho/\rho_s)k' + 2\Delta_0}{2[1 + (\rho/\rho_s)k]} \qquad \text{Eq. (2)}$$

where $\rho$ and $\rho_s$ are the density of fluid and wire, respectively, $\Delta_0$ the internal damping of wire in vacuum and the quantities k and k' are defined as $$k = -1 + 2\Im(A) \qquad \text{Eq. (3)}$$

and $$k' = 2\Re(A) + 2\Delta\Im(A) \qquad \text{Eq. (4)}$$

where $\Re(A)$ and $\Im(A)$ denote taking the real part and imaginary part of complex quantity A, respectively. The complex quantity A in (3) and (4) is given by $$A = (i - \Delta)\left[1 + \frac{2K_1\left[((i-\Delta)\Omega)^{\frac{1}{2}}\right]}{[(i-\Delta)\Omega]^{\frac{1}{2}} K_0\left[((i-\Delta)\Omega)^{\frac{1}{2}}\right]}\right] \qquad \text{Eq. (5)}$$

where $$\Omega = \frac{\omega \rho R^2}{\eta} \qquad \text{Eq. (6)}$$

In Equation (5), $K_0$ and $K_1$ are modified Bessel functions of the second kind and $\Omega$ is related to the Reynolds number that characterizes the flow around the cylindrical wire of radius R at the resonance frequency $\omega$. In some publications it is referred to as the Strouhal length. In Equation (6), the fluid viscosity and density are given by $\eta$ and $\rho$ respectively. For the purpose of clarity, this analysis assumes a strictly Newtonian fluid. However, this in no way limits the applicability of this invention to Newtonian only.

When using an actuating signal having a voltage and current, and a conductive vibrating wire to which this actuating signal is applied, the vibrating wire and any stationary wire or cables used to deliver this actuating signal have an electrical impedance that gives rise to a background voltage so that the measured voltage is not equal to that given by Equation (1), which must be modified to accommodate the finite impedance to give $$V(t) = V_0 e^{-\Delta \omega t} \sin(\omega t + \phi_0) + a + bt \qquad \text{Eq. (7)}$$

where a and b account for the electrical impedance of the wire and also absorb the offset due to unknown background interference. Other background signals may be present as well and the elimination of these background signals will be discussed in greater detail in a subsequent section.

Determination of a parameter such as fluid viscosity requires adjustment of the parameters in equations (2) through (7) so that the calculated and measured response of the vibrating wire are as close as possible within the constraints of the model. This may be achieved by least squares analysis where the optimum characterization of a set of data is one that minimizes the sum of the squares of the deviation of the data from the fitting model (or working equations). The sum of squares of the deviation is closely related to the goodness-of-fit statistic chi-square (or $\chi^2$)

$$\chi^2 = \frac{\sum_{i=1}^{N} |D(t_i) - V(t_i)|^2}{v} \qquad \text{Eq. (8)}$$

where $t_i$ is the time index, $D(t_i)$ and $V(t_i)$ are the recorded transient voltage and the modeled voltage based on the working equations (2) through (7), respectively, and v the number of degrees of freedom for N data points. For a fluid of known density, the least squares criterion is formulated by adjusting the fluid viscosity, $\eta$, to minimize Equation (8) that is $$\min_{\eta, V_0, f, \phi, a, b} \chi^2 \qquad \text{Eq. (9)}$$

in addition to other unknown parameters $V_0$, f, $\phi$, a and b. The Levenberg-Marquardt algorithm may be used to provide a nonlinear regression procedure to solve this minimization problem.

In the minimization of Equation (9), one skilled in the art will recognize that the wire internal damping and wire radius are assumed to be known and provided as input. In practice these physical properties of the wire may be determined to sufficient accuracy by independent methods such as by calibration. Calibration will be further discussed in a subsequent section.

Additionally, the minimization procedure at each iteration also includes solving the logarithmic decrement $\Delta$ which is the root of the following nonlinear equation $$\frac{(\rho/\rho_s)k' + 2\Delta_0}{2[1 + (\rho/\rho_s)k]} - \Delta = 0 \qquad \text{Eq. (10)}$$

When interrogating the sensor in an environment with a high degree of electrical noise, it is advantageous to operate at a higher amplitude. Doing so, however, violates the necessary condition for the validity of equation 1, namely, that the wire amplitude be small compared to its radius. As such, new interpretation was developed to allow the sensor to operate with high precision and high accuracy at an amplitude that was deemed to be suitable for the downhole environment. This amplitude is roughly 10% of the wire radius. The motion of the vibrating wire can be modeled as that of a simple harmonic oscillator with mass m, drag $D_0$, and spring constant k.

$$m\ddot{y}_0 + D_0\dot{y}_0 + ky_0 = 0 \qquad \text{Eq. (11)}$$

However, this equation needs modification when the motion of the wire occurs at high amplitude. The drag $D_0$ in equation 11 will be replaced with a drag that contains a term that is nonlinear in the wire amplitude $A_0$ or position where $\epsilon$ is a constant and $\epsilon A_0^2 \ll 1$.

$$D = D_0(1 + \epsilon A_0^2) \qquad \text{Eq. (12)}$$

The hypothesis that the drag is nonlinear in velocity rather than amplitude results in similar equations albeit with a phase shift. Since phase is a fitting parameter in our current scheme, either methodology would produce acceptable working equations and an accurate measure of viscosity. For simplicity we will focus here on a perturbation involving amplitude. Note that the amplitude and the velocity are linearly proportional to one another.

By incorporating this modified drag equation into the first equation, we arrive at a non-linear equation of motion for the SHO.

$$m\ddot{y} + D_0(1 + \epsilon y^2)\dot{y} + ky = 0 \qquad \text{Eq. (13)}$$

This can be solved by perturbation to determine the following transient signal where the components related to electrical impedance have already been added in.

$$V(t) = V_1 e^{-\Delta \omega t} \sin(\omega t + \phi_1) + V_3 e^{-3\Delta \omega t} \sin(\omega t + \phi_3) + a + bt \qquad \text{Eq. (14)}$$

After fitting the raw signal with equation 14 to determine $\Delta$ regression takes place as described in equations 8-9. As understood by one skilled in the art, a similar interpretation would enable application of the aforementioned method and approach to the interpretation of steady state data having a sufficiently large amplitude. One such example of an environment wherein steady state data with a sufficiently large amplitude may be beneficial is an environment having a high electrical noise component.

These modified equations eliminate a significant systematic error in the viscosity determined from a high amplitude measurement. For example, the systematic error is significant when the viscosity is less than 10 mPa s for a wire of radius 75 micrometers. The viscosity below which the effect is significant depends on physical characteristics of the wire. At viscosities greater than 10 mPa s the damping afforded by the fluid is sufficient to negate the need for these additional terms. These equations are important modifications for the following two reasons: (1), the wire radius is typically determined from measurements of the complex resonance frequency when the wire is immersed in a fluid for which the viscosity is known from independent sources with sufficient certainty; and (2), the fluids that flow in boreholes and tools have viscosities on the order of 1 mPa s. For item 1, the fluids used are often low viscosity fluids such as methylbenzene or water and this effect needs to be properly taken account.

As set forth previously, an alternate embodiment of the present invention may utilize an actuating signal applied in the presence of an electromagnetic field, wherein the actuating signal is a steady state signal. This steady state signal may be generated by passing an alternating current through at least a portion of the vibrating wire. Using this steady state drive mechanism, fluid parameters may be extracted.

In accordance with the aforementioned alternative embodiment, in a steady state mode or drive mechanism, the vibrating wire 204 is placed in a magnetic field and it is driven in transverse oscillations by passing an alternating current. The voltage across the wire is given by, $$V = V_1 + V_2, \qquad \text{Eq. (15)}$$

where $V_1$ is the voltage arising from the electrical impedance of the effectively stationary wire while $V_2$ represents the motional emf. $V_1$ is represented empirically by, $$V_1 = a + ib + icf, \qquad \text{Eq. (16)}$$

where f is the frequency at which the wire is driven, and a, b, and c are adjustable parameters that account for the electrical impedance of the wire and absorb the offset used in the lock-in amplifier to ensure the voltage signal is detected in the most sensitive range. In equation 16, a, b, and c are adjustable parameters determined by regression with the measured complex voltage. $V_2$, given by $$V_2 = \frac{Afi}{f_0^2 - (1+\beta)f^2 + (\beta' + 2\Delta_0)f^2 i}, \qquad \text{Eq. (17)}$$

relates the measured quantity to the fluid properties. In equation 17, $\Lambda$ is an amplitude, $f_0$ the resonance frequency of the wire in vacuum, $\Delta_0$ the internal damping of the wire, $\beta$ the added mass arising from the fluid displaced by the wire, and $\beta'$ the damping due to the fluid viscosity. Defining $\beta$ and $\beta'$ below:

$$\beta = k\frac{\rho}{\rho_s} \qquad \text{Eq. (18)}$$

$$\beta' = k'\frac{\rho}{\rho_s} \qquad \text{Eq. (19)}$$

Experimental comparative results obtained using a steady state drive mechanism and a transient drive mechanism indicate that the fluid parameters measured are in close agreement using the embodiments recited herein. One skilled in the art will therefore recognize that the selection of an appropriate drive mechanism may be governed by the anticipated fluid parameter(s) measured, the operating environment and the fluid within the fluid channel.

Figure 3A:
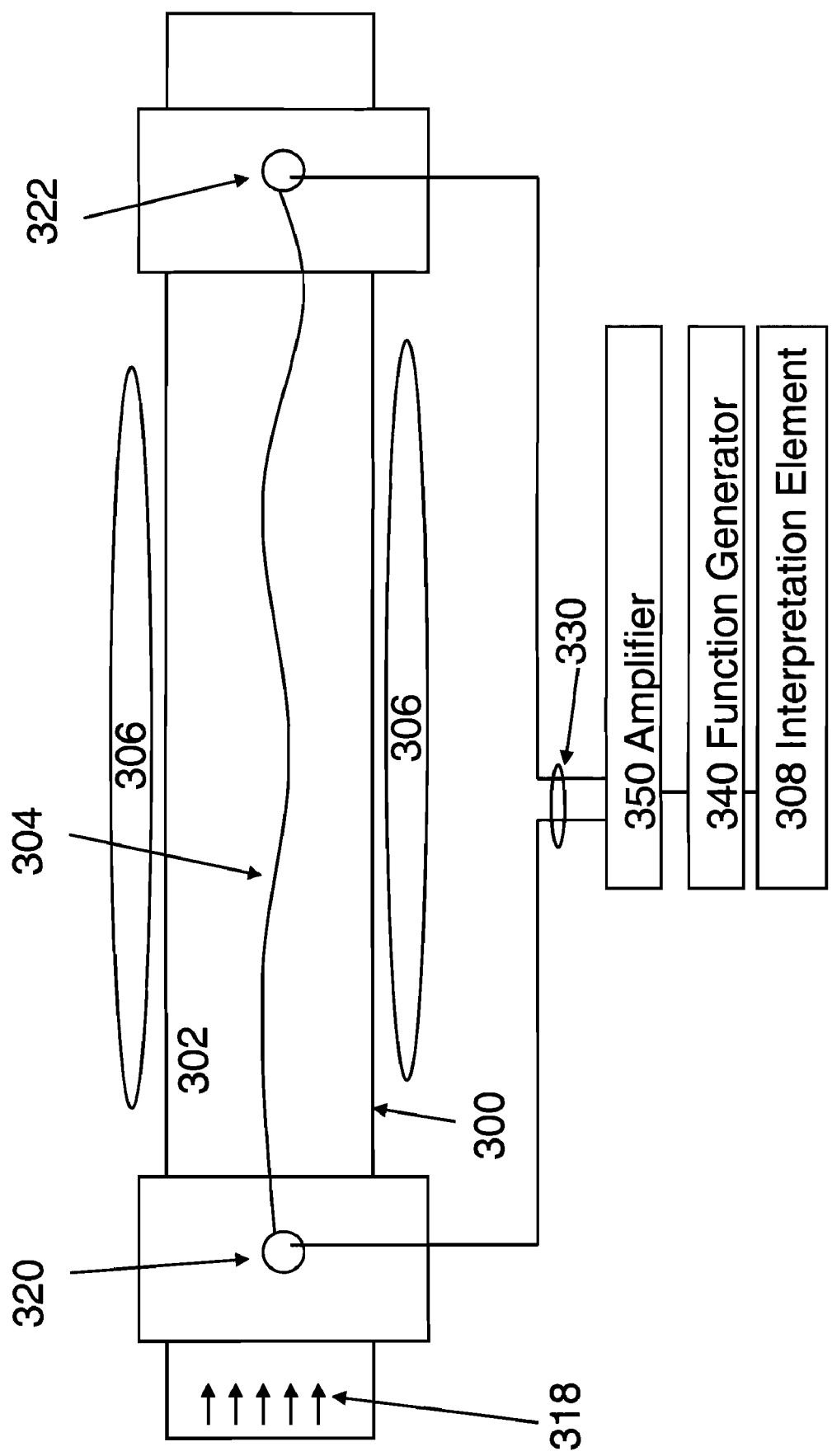
FIG. 3A is an illustrative embodiment of a suitable resonating element for use in practicing an embodiment of the present invention (steady state)
Figure 3B:
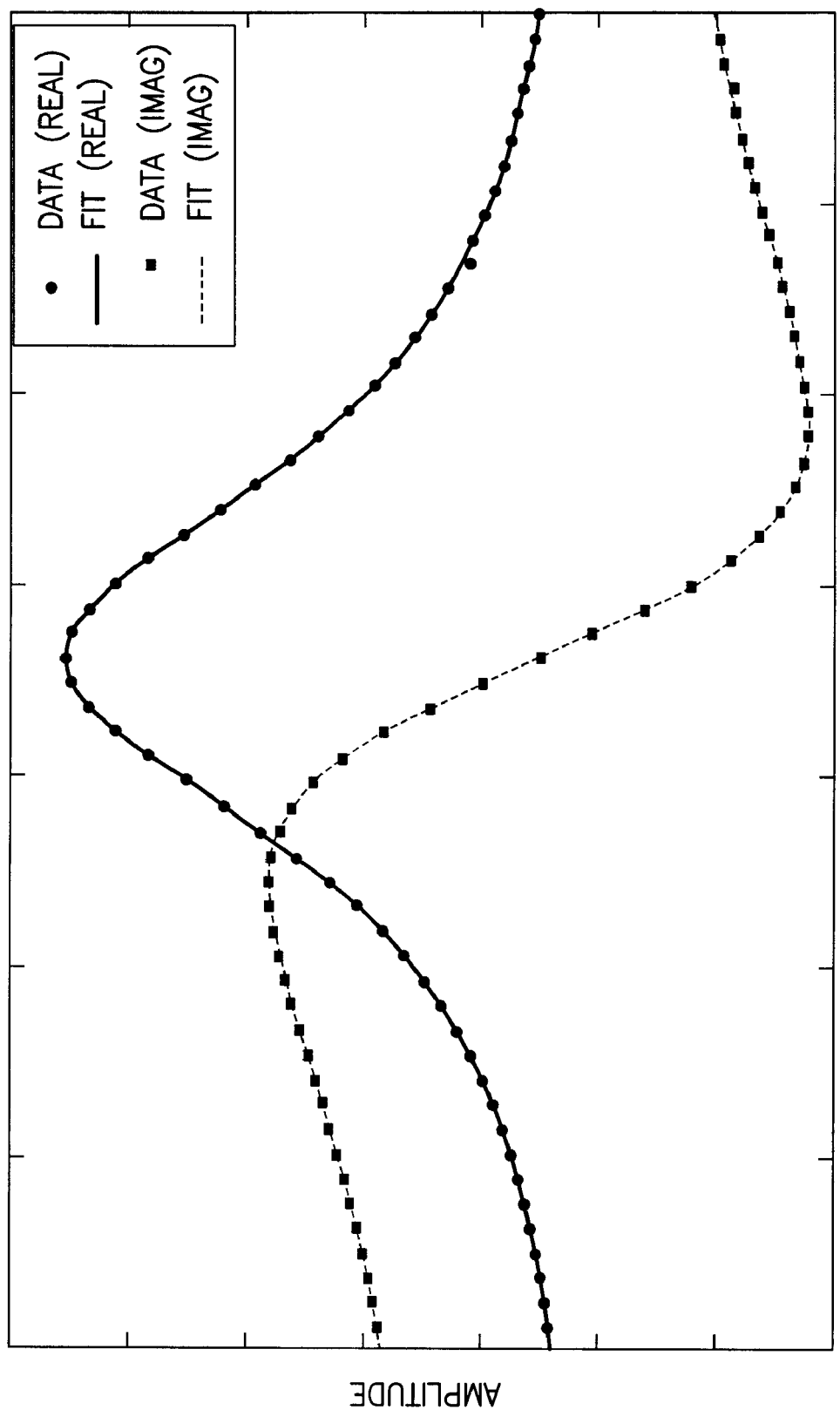
FIG. 3B is a graphical representation of the typical deflection exhibited by an embodiment of the present invention as a function of frequency wherein steady state data is analyzed.

FIG. 3A is a graphical representation of the present invention when using steady state data. As depicted in FIG. 3A, a fluid channel 300 containing a fluid 302 with a fluid direction 318 is illustrated. Within the fluid channel 300 is a vibrating wire 304 disposed between two holders 320, 322 such that the vibrating wire is in tensions. Although not illustrated, the vibrating wire 304 of the present invention will be deemed to be electrically conductive. In communication with the holders 320, 322 are electrical connections 330 such that a steady state signal provided by a function generator 340 and amplified 350 may be delivered to the vibrating wire 304. A suitable steady state signal is illustrated in FIG. 3B. Further associated with the vibrating wire 304, and in electrical communication using the aforementioned electrical connections 330 is an interpretation element 308 capable of providing, e.g., identifying or determining, a fluid parameter of a fluid within the flow channel 300. The interpretation element 308 of the present invention may take numerous forms, as understood by one skilled in the art, such that the aforementioned equations and embodiment for determining a fluid parameter may be practiced. In accordance with one embodiment of the present invention, the interpretation element 308 may be implemented in software, hardware or some combination therefore.

In accordance with the present embodiment, the displacement of the vibrating wire due to the actuation element may create a motional emf that can be measured by the interpretation element 308. This measured signal may be utilizes in combination with the transient equations set forth above to determine a parameter such as viscosity.

Figure 4A:
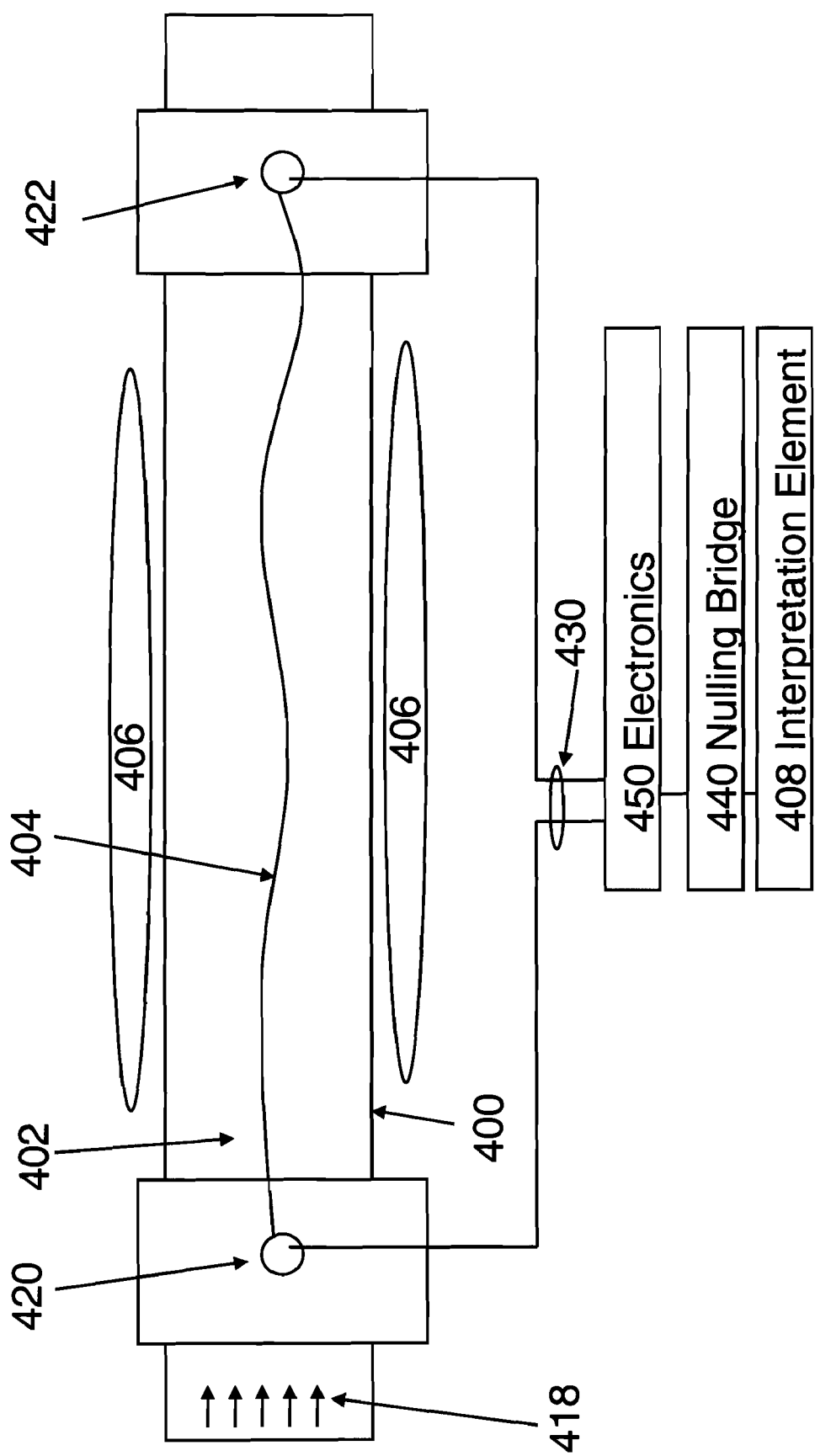
FIG. 4A is an illustrative embodiment of a suitable resonating element for use in practicing an embodiment of the present invention (transient)
Figure 4B:
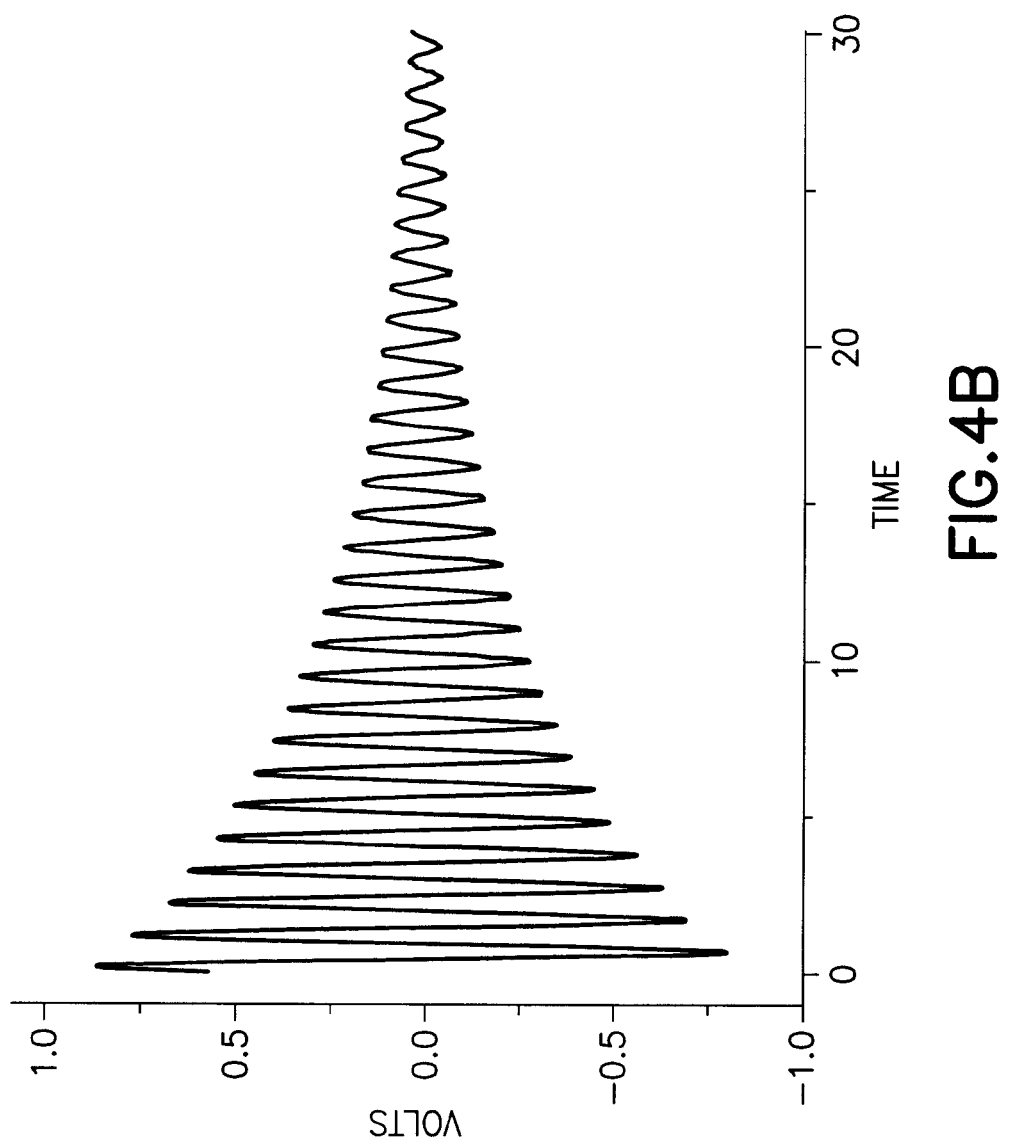
FIG. 4B is a graphical representation of the typical deflection exhibited by an embodiment of the present invention as a function of time wherein transient data is analyzed.

FIG. 4A is a graphical representation of the present invention when using transient data. As depicted in FIG. 4A, a fluid channel 400 containing a fluid 402 with a fluid direction 418 is illustrated. Within the fluid channel 400 is a vibrating wire 404 disposed between two holders 420, 422 such that the vibrating wire is in tension. Although not illustrated, the vibrating wire 404 of the present invention will be deemed to be electrically conductive. In communication with the holders 420, 422 are electrical connections 430 such that a transient signal provided by a nulling bridge 440 and electronics 450 may be delivered to the vibrating wire 404. A suitable transient signal is illustrated in FIG. 4B.

Further associated with the vibrating wire 404, and in electrical communication using the aforementioned electrical connections 430 is an interpretation element 408 capable of providing, e.g., identifying or determining, a fluid parameter of a fluid within the flow channel 400. The signal generated by the wire moving in the presence of a magnetic field generates a motional emf that can be measured by the interpretation element 408 such that the time required for the signal amplitude of the measured motivational emf to decrease is used to determine a parameter such as viscosity in accordance with the steady state equations above. The interpretation element 408 may record the motivational emf for a fixed period of time, wherein this period is related to the viscosity of the fluid in the flow channel 400. For example, the time period for which the motional emf signal is acquired may be increased in gases where the viscosity would be lower as compared to liquid. The interpretation element 408 of the present invention may take numerous forms, as understood by one skilled in the art, such that the aforementioned equations and embodiment for determining a fluid parameter may be practiced. In accordance with one embodiment of the present invention, the interpretation element 408 may be implemented in software, hardware or some combination therefore. Additionally, the wire diameter and internal damping factor noted previously may be determined by calibration prior to commencing measurements.

Background Signal Compensation

As set forth above, one embodiment of the present invention may be practiced using a steady state drive mechanism, a transient drive mechanism, or some combination thereof. Regardless of drive mechanism, the accuracy of the parameter measurement of the vibrating wire of the present invention may be degraded due to background effects of the apparatus. For example, background effects in the present invention may be attributed to a variety of factors, including but not limited to the selected excitation and displacement frequency utilized, as well as error introduced by the associated hardware necessary to practice various embodiments of the present invention. For example, wiring and cabling 430 between the vibrating wire 404 and the electronics 450 illustrated in FIG. 4A may introduce errors due to impedance in this wiring 430. Additionally, nearby electronics and limited component and wiring isolation may introduce undesirable signals and the measured signal may be deformed to such an extent that it is impossible to accurately measure $\Delta$ from the raw signal. In settings such as these, background elimination provided a means to compensate for background effects and in turn allows for increased accuracy in the parameter measured.

Figure 5:
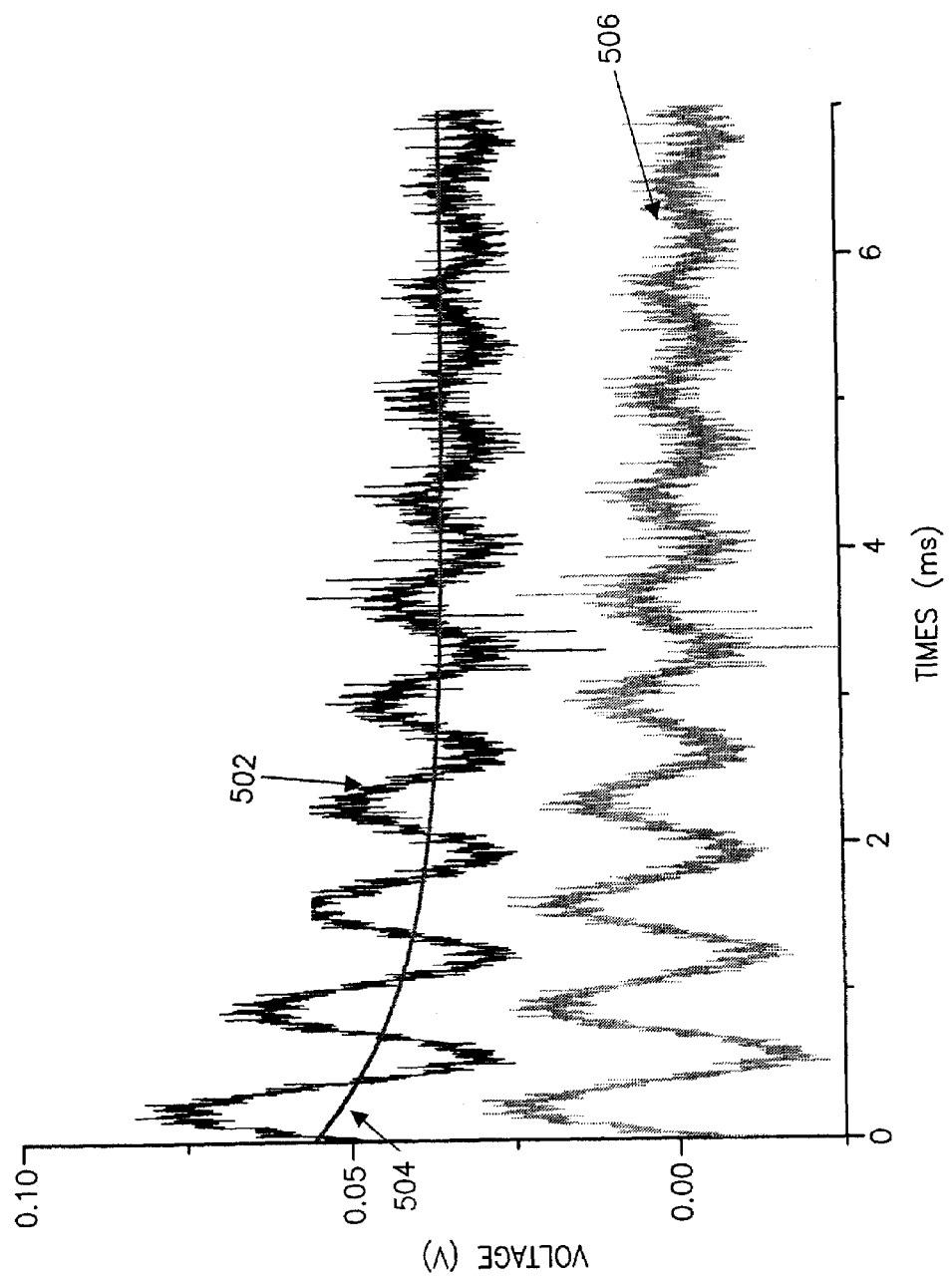
FIG. 5 is an example of a graphical depiction of a ringdown riding on top of an unwanted slow exponential decay. Further illustrated is the pure exponential decay.

In accordance with one embodiment of the present invention, background effects may be minimized or compensated for by exciting the vibrating wire at a frequency far away from the resonance frequency. As illustrated in FIG. 5, the unprocessed signal (502) consists of a sinusoidal oscillation riding on top of an exponent decay plus an offset. In accordance with the present embodiment, the vibrating wire is excited at the resonance frequency $f_0$, the signal is measured and recorded 502, and then the vibrating wire is excited at a frequency equaling $f_0$ plus approximately ten or more times the bandwidth where the oscillatory portion of the signal is minimal. This background signal (504) is illustrated wherein the vibrating wire was excited far from resonance such that only the exponential decay is present in the signal. In the present embodiment, the response measured at a frequency far from that of the resonance is a measure of the background signal, wherein this signal can be assumed to be independent of frequency and subtracted from or divided by the emf at other frequencies. The difference or quotient of these two signals provides a signal with the background largely eliminated 506.

Figure 6:
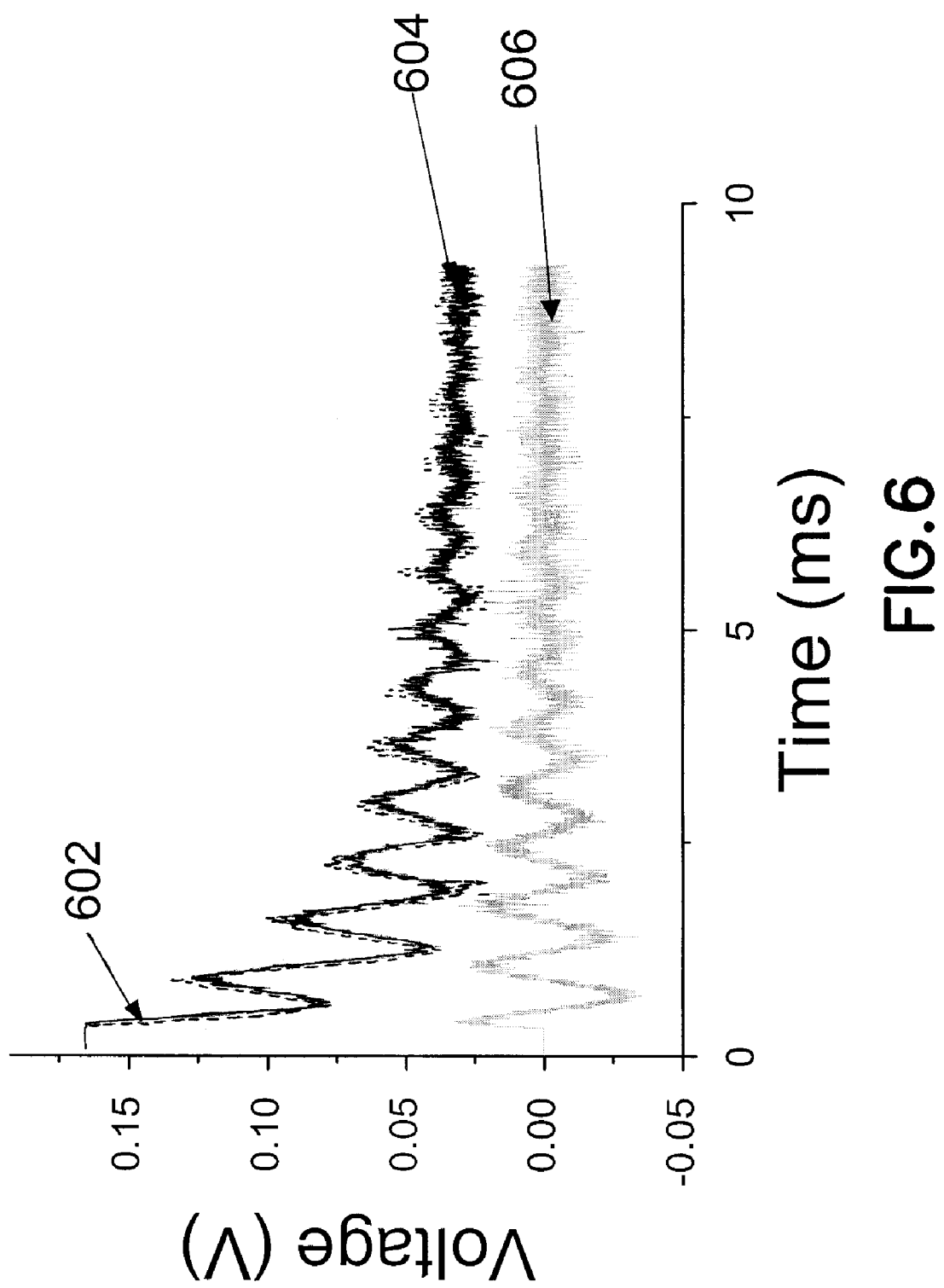
FIG. 6 is a graphical depiction of ringdown.

In accordance with an alternative background elimination technique, the background signal may be measured by exciting the vibrating wire near the resonance frequency. Such an example is illustrated in FIG. 6, wherein the vibrating wire is first excited at the resonance frequency $f_0$=1450.8 Hz (602). In accordance with this embodiment, the signal is measured and recorded and then the vibrating wire is excited at a second frequency equaling $f_0$ plus the bandwidth. (604). In the present example, this second frequency is equal to 1500 Hz. The difference of these two signals produces a third signal (606) which is largely free of artifacts.

In the present embodiment, the optimum frequency for background elimination (the second frequency) was determined experimentally for the particular wire, clamping arrangement, electronics and interconnecting cables. Such a determination is not intended to be limiting in scope, as the preferred frequency for background elimination may be determined via a variety of alternative means.

In accordance with an alternative embodiment of the present invention, background elimination may be practiced using regression alone. In accordance with this embodiment, proper fitting of a signal with an added polynomial component allows for the transient to be properly isolated. For example, by adding $$a+bt \quad \text{Eq. (20)}$$

an offset (a) plus a component increasing or decreasing in time (b) can be eliminated. Higher orders can be added as need be. Additionally, background signal may be eliminated by alternative techniques as understood by one skilled in the art. For example, the background signal may be eliminated by inversion of the excitation phase. For example, background elimination may be achieved by excitation at the resonance frequency of the vibrating wire but with the excitation signal phase shifted by π radians. The difference between the signal measured via the original excitation and that measured by the phase shifted excitation will consist of a background free signal.

One skilled in the art will readily recognize that the aforementioned techniques for background elimination are not exhaustive. These recited techniques are for illustrative purposes alone, and may be practiced using steady state data, transient date, or some combination thereof. Additionally, these background techniques recited herein may be utilized either alone or in combination with additional techniques known by one skilled in the art. Finally, depending in part upon the parameter to be measured, the vibrating wire arrangement, and the associated electronics, one suitable background elimination technique may be more appropriate such that the resulting parameter measurement offers increased accuracy.

Figure 7:
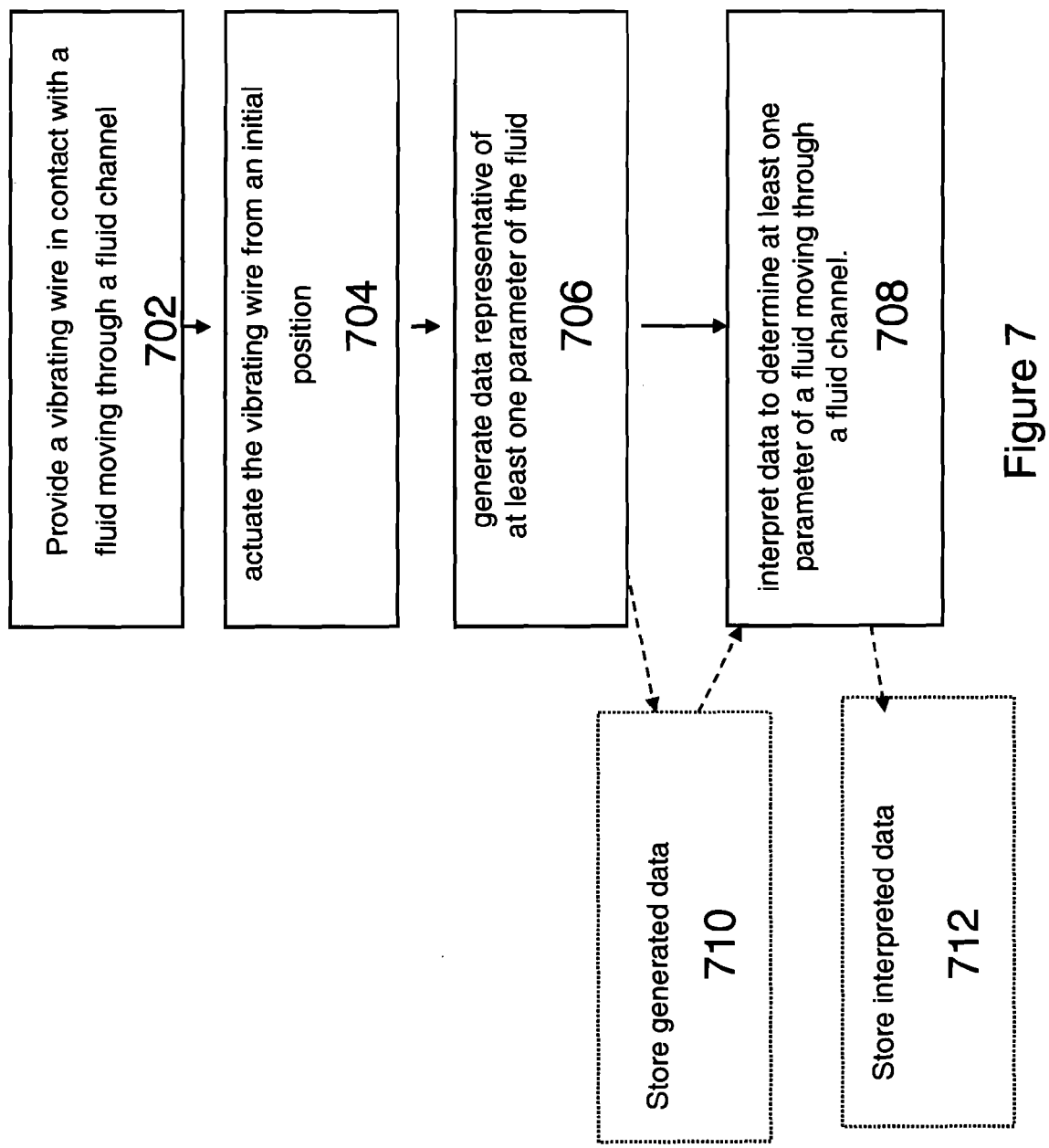
FIG. 7 is an illustrative flowchart of a method for practicing one embodiment of the present invention.

FIG. 7 is a flowchart illustrating the steps necessary to practice one embodiment of the present invention. In accordance with the present embodiment, a vibrating wire in contact with a fluid moving through a fluid channel is provided (step 702). The vibrating wire is then actuated from an initial position, or equilibrium position (step 704). As set forth prior, actuation may be via a variety of means understood by one skilled in the art, including but not limited to the application of an actuation signal to at least a portion of the vibrating wire in the presence of an electromagnetic field. The actuation signal may be an electrical signal applied to a conductive vibrating wire, wherein the electrical signal is a steady state signal, a transient signal or some combination thereof. Upon actuation of the vibrating wire (704) data representative of at least one parameter of the fluid is generated (step 706) wherein this data is interpreted to provide, e.g., identify or determine, at least one parameter of the fluid moving through the fluid channel (708). Alternative embodiments of the present invention may further include the steps of storing data representative of at least one parameter of a fluid (710) or storing interpreted data (712) as understood by one skilled in the art. The storage of data in accordance with one embodiment may be via a variety of suitable forms, including storage in an electronic form or mechanical form as understood by one skilled in the art. Additionally, interpretation of data in accordance with step 708 may occur using a variety of hardware or software components or some combination thereof. One suitable device for practicing aspects of the present invention is illustrated in FIG. 8.

Figure 8:
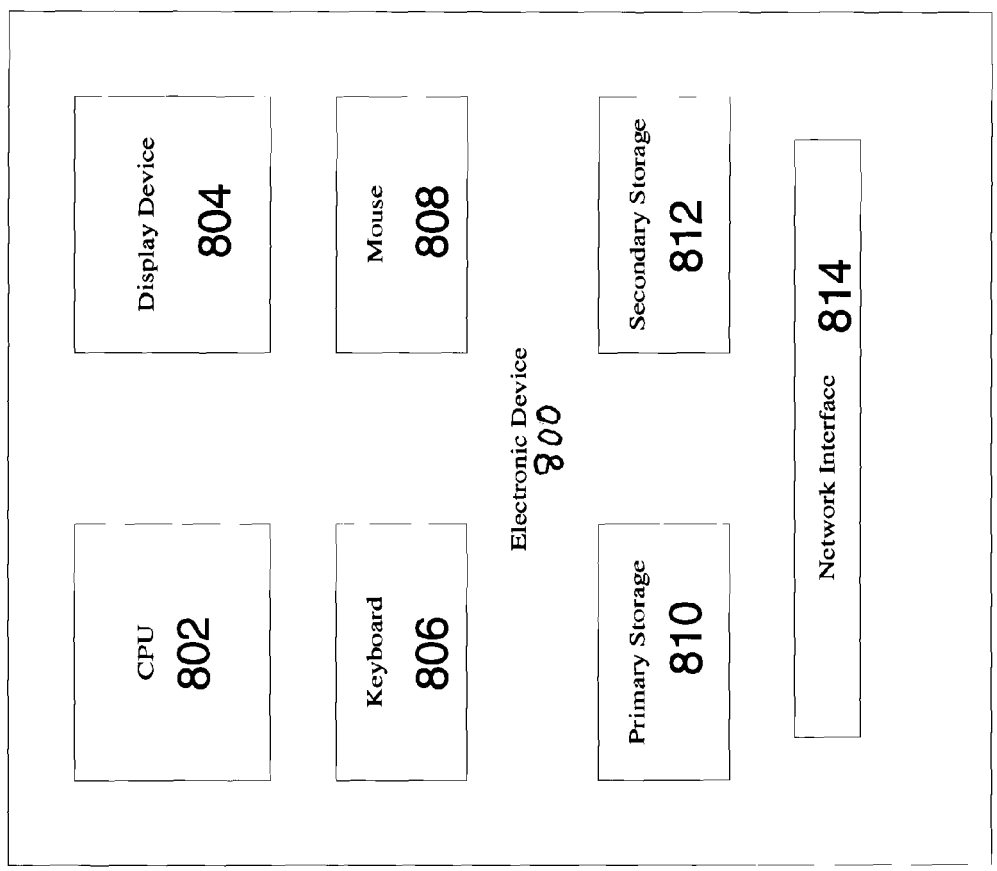
FIG. 8 is an illustrative depiction of one embodiment suitable for practicing aspects of the invention.

FIG. 8 illustrates one example embodiment of an electronic device 800 suitable for practicing at least a portion of one or more aspects of the illustrative embodiments of the present invention. The electronic device 800 is representative of a number of different technologies, such as personal computers (PCs), laptop computers, workstations, personal digital assistants (PDAs), Internet appliances, cellular telephones, and the like. In the illustrated embodiment, the electronic device 800 includes a central processing unit (CPU) 802 and may further include a display device 804. The display device 804 enables the electronic device 800 to communicate directly with a user through a visual display. The electronic device 800 further may include a keyboard 806 and a mouse 808. Other potential input devices not depicted include a stylus, trackball, joystick, touch pad, touch screen, and the like. The electronic device 800 includes primary storage 810 and secondary storage 812 for storing data and instructions, wherein the primary storage 810 and secondary storage 812 may take numerous forms as understood by one skilled in the art. The storage devices 810 and 812 can include such technologies as a floppy drive, hard drive, tape drive, optical drive, read only memory (ROM), random access memory (RAM), virtual memory, graphical memory and the like. A variety of suitable applications and utilities can be resident on one or both of the storage devices 810 and/or 812. The electronic device 800 can also include a network interface 814 for communicating with one or more electronic devices external to the electronic device 800 depicted, or for communication with individual components of the electronic device 800 located externally. The CPU 802 has either internally, or externally, attached thereto one or more of the aforementioned components.

It should be noted that the electronic device 800 is merely representative of a structure for implementing the present invention. However, one of ordinary skill in the art will appreciate that the present invention is not limited to implementation on only the described device 800. Other implementations can be utilized, including an implementation based partially or entirely in embedded code, where no user inputs or display devices are necessary. Rather, a processor can communicate directly with another processor or other device.

Calibration Methodologies

In accordance with the present invention, various calibration methods may be employed. For example, the wire internal damping can be determined with the transient data collected in vacuum and the wire radius, R, can be determined from the transient data collected in a calibration fluid for which the viscosity and density are known. One calibration embodiment for calibrating the vibrating wire includes the following two steps:

Calibration of Wire Internal Damping in Vacuum—The fluid viscosity ($\eta$) and density ($\rho$) in the working equations (1)-(9) are set to zero and therefore, the induced voltage V is given by:

$$V(t) = V_0 e^{-\Delta_0 \omega t} \sin(\omega t + \phi_0) \qquad \text{Eq. (21)}$$

Since $\beta=0$ and $\beta'=0$, the only damping factor in Eq. 17 is $\Delta_0$. The wire internal damping is obtained by fitting the vacuum data with Eq. 1. The wire radius does not enter Eq. 21 and therefore, the internal damping factor $\Delta_0$ can be determined without knowledge of the wire radius. Only an order of magnitude estimate of the damping factor is required to determine the viscosity of liquids with wires that have diameters on the order of 0.1 mm. For the purpose of our discussion, with wires of 0.1 mm diameter and resonance frequencies on the order of 1 kHz the viscosity of a liquid is defined by 1 mPa s.

Calibration of wire radius with known calibration fluid—The wire radius, R, is determined from the data collected in a calibration fluid for which the viscosity and density are known. The determination of wire radius requires data fitting with the working equations (1)-(9) of vibrating wire, with the internal damping $\Delta_0$ known and obtained in the previous step.

Acquisition of vibrating wire data in vacuum would require some special hardware (e.g. vacuum pump and sealed chamber) to be built and the procedure would be tedious and time-consuming. Moreover this would not be practical in many oil field locations. It is conceivably easier if one can replace the data acquired in vacuum with the data acquired in air (or another readily available fluid) for the calibration purpose. However, the effect of added mass and viscous damping due to air (although small) is not negligible and would introduce a systematic error in the value for internal damping. This error in the internal damping could consequently produce a significant error when the sensor is used to measure the viscosity of gas. Furthermore, the error in the internal damping would also propagate into the estimate of wire radius.

An alternative calibration method in accordance with one embodiment of the present invention may include an iterative approach to calibration that determines the internal damping factor and wire radius. The input consists of the data sets collected in air and in a calibration fluid for which the viscosity and density are known. The iterative algorithm is described as follows:

1. Set the initial estimate of R to the nominal value provided by supplier.
2. Obtain the estimate of $\Delta_0$ by fitting the air data with working equations (1)-(10), with the known air density, air viscosity and the most recent estimate of R.
3. Obtain the estimate of R by fitting the fluid data with working equations (1)-(10), with the known fluid density, fluid viscosity and the most recent estimate of $\Delta_0$.
4. Go back to step 2 for the next iteration.

Generally, the algorithm would converge to the correct internal damping $\Delta_0$ and wire radius R in a few iterations.

The foregoing description is presented for purposes of illustration and description, and is not intended to limit the invention in the form disclosed herein. Consequently, variations and modifications to the inventive parameter measurement systems and methods described commensurate with the above teachings, and the teachings of the relevant art, are deemed within the scope of this invention. These variations will readily suggest themselves to those skilled in the relevant oilfield, fluid analysis, and other relevant industrial art, and are encompassed within the spirit of the invention and the scope of the following claims. Moreover, the embodiments described are further intended to explain the best mode for practicing the invention, and to enable others skilled in the art to utilize the invention in such, or other, embodiments, and with various modifications required by the particular applications or uses of the invention. It is intended that the appended claims be construed to include all alternative embodiments to the extent that it is permitted in view of the applicable prior art.

What is claimed is:

1. A measurement apparatus for determining at least one parameter of a fluid moving through a fluid channel, comprising:
   a vibrating wire clamped under tension and in contact with the fluid moving through the fluid channel;
   an actuating device capable of displacing the vibrating wire, when motion on the vibrating wire occurs a physical amplitude greater than 10 percent of a radius of the vibrating wire generates a drag data; and
   an interpretation element capable of determining the at least one parameter of the fluid moving through the fluid channel based upon data received from the vibrating wire upon actuation by the actuating device, wherein the received data includes the generated drag data.

2. The measurement apparatus of claim 1, wherein said vibrating wire is electrically conductive.

3. The measurement apparatus of claim 1, wherein said actuating device further provides an electromagnetic field and an actuation signal.

4. The measurement apparatus of claim 3, wherein said electromagnetic field is provided in the vicinity of the vibrating wire.

5. The measurement apparatus of claim 3, wherein said actuation signal is provided to at least a portion of the vibrating wire.

6. The measurement apparatus of claim 3, wherein said actuation signal is a steady state signal.

7. The measurement apparatus of claim 6, wherein said steady state signal is provided by passing an alternating current through at least a portion of the vibrating wire.

8. The measurement apparatus of claim 3, wherein said actuation signal is a transient signal.

9. The measurement apparatus of claim 8, wherein said transient signal is provided by passing a burst of alternating current through at least a portion of the vibrating wire.

10. The measurement apparatus of claim 8, wherein said transient signal is provided by passing a direct current signal through at least a portion of the vibrating wire.

11. The measurement apparatus of claim 1, wherein said at least one parameter is fluid density.

12. The measurement apparatus of claim 1, wherein said at least one parameter is fluid viscosity.

13. The measurement apparatus of claim 1, wherein said fluid channel is a microfluidic channel.

14. The measurement apparatus of claim 1, wherein said measurement apparatus may be incorporated into a microfluidic platform.

15. The measurement apparatus of claim 1, wherein the drag data consists of a drag on the vibrating wire that depends non-linearly on a velocity of the vibrating wire normal to its axis when the vibrating wire is displaced at the physical amplitude greater than 10% of the radius of the vibrating wire.

16. A method for determining at least one parameter of a fluid moving through a fluid channel, the method comprising the steps of:
- having a vibrating wire, wherein said vibrating wire is in contact with the fluid moving through the fluid channel;
- actuating said vibrating wire to provide motion on the vibrating wire so a physical amplitude greater than 10 percent of a radius of the vibrating wire occurs;
- generating data representative of the at least one parameter of the fluid; and
- interpreting said generated data to determine the at least one parameter of the fluid moving through the fluid channel.

17. The method of claim 16, further comprising the step of storing said generated data.

18. The method of claim 16, wherein said vibrating wire is electrically conductive.

19. The method of claim 16, wherein the step of actuating the vibrating wire further includes providing an actuation signal to at least a portion of the vibrating wire in the presence of an electromagnetic field.

20. The method of claim 19, wherein said actuation signal is a steady state signal.

21. The method of claim 20, wherein said steady state signal is provided by passing an alternating current through at least a portion of the vibrating wire.

22. The method of claim 19, wherein said actuation signal is a transient signal.

23. The method of claim 22, wherein said transient signal is provided by passing a burst of alternating current through at least a portion of the vibrating wire.

24. The method of claim 22, wherein said transient signal is provided by passing a direct current signal through at least a portion of the vibrating wire.

25. The method of claim 16, wherein interpreting the data further comprises the step of compensating a background signal.

26. The method of claim 25, wherein said step of compensating for the background signal further comprises exciting the vibrating wire at a frequency that is not equal to a resonant frequency so as to provide a resonant signal.

27. The method of claim 26, further comprising the step of calculating a quotient of the resonant signal of the vibrating wire and the background signal.

28. The method of claim 25, wherein said step of compensating for the background signal further comprises exciting the vibrating wire at a frequency approximate the resonance frequency to determine the background signal.

29. The method of claim 25, wherein said step of compensating for the background signal further comprises eliminating the background signal using regression.

30. The method of claim 16, wherein said at least one parameter is fluid density.

31. The method of claim 16, wherein said at least one parameter is fluid viscosity.

32. The method of claim 16, further comprising the step of calibrating said vibrating wire to allow for accurate measurement of the at least one parameter of the fluid moving through the fluid channel.

33. A measurement apparatus for identifying or determining at least one parameter of a fluid moving through a fluid channel, the measurement apparatus comprising:
- a vibrating wire clamped under tension and in contact with the fluid moving through the fluid channel;
- an actuating device capable of displacing the vibrating wire from an initial position; and
- an interpretation element having a means for background signal elimination, such that the interpretation element is capable of identifying or determining the at least one parameter of the fluid moving through the fluid channel based upon data received from the vibrating wire upon actuation by the actuating device.

* * * * *